(12) United States Patent
Miranda et al.

(10) Patent No.: US 12,249,009 B2
(45) Date of Patent: Mar. 11, 2025

(54) MOTION COMPENSATION OF POSITRON EMISSION TOMOGRAPHIC DATA

(71) Applicant: UNIVERSITEIT ANTWERPEN, Antwerp (BE)

(72) Inventors: Alan Miranda, Antwerp (BE); Jeroen Verhaeghe, Antwerp (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 331 days.

(21) Appl. No.: 17/779,601

(22) PCT Filed: Nov. 23, 2020

(86) PCT No.: PCT/EP2020/083050
§ 371 (c)(1),
(2) Date: May 25, 2022

(87) PCT Pub. No.: WO2021/105056
PCT Pub. Date: Jun. 3, 2021

(65) Prior Publication Data
US 2023/0008263 A1    Jan. 12, 2023

(30) Foreign Application Priority Data

Nov. 27, 2019 (EP) .................... 19211752

(51) Int. Cl.
*G06T 11/00* (2006.01)
*A61B 6/03* (2006.01)
*G01T 1/29* (2006.01)

(52) U.S. Cl.
CPC ............ *G06T 11/008* (2013.01); *A61B 6/037* (2013.01); *G01T 1/2985* (2013.01)

(58) Field of Classification Search
CPC ...... G01T 1/2985; A61B 6/037; G06T 11/008
See application file for complete search history.

(56) References Cited

U.S. PATENT DOCUMENTS

| | | | |
|---|---|---|---|
| 10,438,349 B2 | 10/2019 | Yu et al. | |
| 10,593,052 B2 | 3/2020 | Abhari et al. | |
| 2016/0206272 A1 | 7/2016 | Kyriakou | |
| 2017/0032538 A1 | 2/2017 | Ernst et al. | |

(Continued)

FOREIGN PATENT DOCUMENTS

WO    2010109348 A2    9/2010

OTHER PUBLICATIONS

Sun, Tao et al., "Body Motion Detection and Correction in Cardiac PET: Phantom and Human Studies.", Medical physics (Lancaster) 46.11 (2019): 4898-4906. (Year: 2019).*

(Continued)

*Primary Examiner* — John R Wallace
(74) *Attorney, Agent, or Firm* — Workman Nydegger (57) ABSTRACT

A method for compensating motion in positron emission tomographic, PET, data comprising coincident lines of response from positron-emitting position markers, includes: detecting a slippage of one or more of the position markers; determining slippage correction parameters based on the detected slippage; and applying motion correction to the PET data by taking into account the slippage correction parameters, thereby obtaining a motion-compensated PET data.

9 Claims, 6 Drawing Sheets

— 601

— 602

Scaling the scatter sinogram with respect to the PET sinogram, thereby obtaining scatter corrected motion-compensated PET data

— 603

(56) References Cited

U.S. PATENT DOCUMENTS

2018/0325415 A1  11/2018  Ehrl et al.

OTHER PUBLICATIONS

Lu, Yihuan et al., "Data-Driven Voluntary Body Motion Detection and Non-Rigid Event-by-Event Correction for Static and Dynamic PET.", Physics in medicine & biology 64.6 (2019): 065002. (Year: 2019).*

Extended European Search Report from corresponding EP Application No. 19211752.1, May 20, 2020.

International Search Report from corresponding PCT Application No. PCT/EP2020/083050, Feb. 16, 2021.

* cited by examiner

MOTION COMPENSATION OF POSITRON EMISSION TOMOGRAPHIC DATA

TECHNICAL FIELD

Various example embodiments relate to the compensation of motion in positron emission tomographic, PET, data.

BACKGROUND

Positron emission tomography, PET, is used to image physiological and biochemical processes (e.g. glucose metabolism) in vivo in humans and animals. This imaging technique is a gold standard method for quantifying neurochemistry and molecular processes directly in the brain by injecting a radiopharmaceutical that specifically targets the processes of interest.

Patient movements during the medical imaging, however, results in a degraded image quality and a reduced diagnostic confidence. Examples of sources of patient movements are head and neck movements and respiratory motion.

An example of a conventional solution to correct for patient movement consists of recording motion data from one or more electronic devices, e.g. a camera, during the acquiring of the PET data. Motion correction is performed through post-processing of the PET data by correlating the PET data with the motion data. In addition to the increased complexity of the imaging system, i.e. a PET scanner and one or more camera devices, the recorded data usually lacks accuracy. Further, delays between the recorded motion data and the acquired PET data may be present. Furthermore, patients may find such video recording invasive. In general, such motion correction methods are invasive, complex and moreover result in an inaccurate and erroneous motion correction.

US2017/0032538 A1 discloses a motion correction technique accounting for false movements in motion correction systems used in conjunction with medical imaging and/or therapeutic systems. The described motion correction technique detects false movements so that such false movements are not accounted for in the motion correction process.

SUMMARY

The scope of protection sought for various embodiments of the invention is set out by the independent claims.

The embodiments and features described in this specification that do not fall within the scope of the independent claims, if any, are to be interpreted as examples useful for understanding various embodiments of the invention.

An object of embodiments of the present disclosure is to provide a method for correcting motion in PET data allowing to obtain high quality reconstructed images and to improve the diagnostic confidence.

This object is achieved, according to a first example aspect of the present disclosure, by a method for compensating motion in positron emission tomographic, PET, data, comprising coincident lines of response from positron-emitting position markers, the method comprising:
  detecting a slippage of one or more of the position markers;
  determining slippage correction parameters based on the detected slippage; and
  applying motion correction to the PET data by taking into account the slippage correction parameters, thereby obtaining a motion-compensated PET data.

By placing position marker on the subject, the movements of the subject can be tracked during the acquisition of the PET data. The position markers may be external emitting sources, such as positron emitting sources. Such position markers may have low-activity (or dose) and may be prepared using short-lived isotopes, e.g. Fluorine-18 and Carbon-11.

Motion correction (or motion compensation) is performed through post-processing of the PET data by tracking the position markers to derive the movement of the subject being scanned. However, the position markers may slip during the scanning due to a number of factors, such as skin flexibility, skin moisture or due to the subject movement itself (e.g. scratching). If the slippage is undetected the motion-compensated PET data is erroneous and inaccurate.

The proposed method herein performs motion correction of the PET data while considering the detected slippage of one or more position markers. The method detects the slippage of the one or more position markers. Based on the detected slippage the method derives slippage correction parameters and takes them into account when performing the motion compensation of the PET data. In this way a simpler, non-intrusive and, most of all, an accurate and free from errors motion-compensated PET data is obtained.

According to an example embodiment, the method further comprising deriving a plurality of images from the PET data, and, identifying therefrom, based on the detected slippage, a first set of images before the detected slippage and a second set of images after the detected slippage.

The corresponding set of images include images with subject movement free from slippage, wherein the movement identified between the sets of images represents the slippage of the one or more position markers. This allows to differentiate between patient movement and slippage of the one or more position markers. This enables accurate estimation of the patient movement as well as accurate estimation of the slippage of the position markers.

According to an example embodiment, the identifying comprises determining locations of the position markers in the images and calculating therefrom inter-point distances between the position markers in the images.

Based on the detected locations of the position markers, inter-point distances between them is determined. This allows to derive the position of the subject in the corresponding images. By comparing the detected position, i.e. the inter-point distances among subsequent images, the movement of the subject is derived.

According to example embodiments, the identifying further comprises clustering the calculated inter-point distances between the position markers in the images into a first set before slippage and a second set after slippage.

By clustering the inter-point distances the slippage of one or more position markers is identified in an efficient and a robust manner.

According to example embodiments, the clustering can be performed by applying an unsupervised clustering algorithm, such as the expectation-maximization (i.e. a soft assignment clustering) or k-means (i.e. a hard assignment clustering). Preferably, k-means clustering algorithms is applied.

By identifying which inter-point distances of a respective set of inter-point distances corresponds to which image, it is possible to identify a first set of images before the slippage and a second set of images after the slippage. The two set of images therefore contain motion information originating from the patient movement.

According to an exemplary embodiment, the method further comprising:
    deriving motion correction parameters for the first and second set of images;
    applying the derived motion compensation parameters to the respective set of images, thereby obtaining a first and a second motion-compensated set of images from the respective first and second set of images.

By deriving the motion correction parameters for a respective set of images, the derived motion correction parameters will not suffer from any artefacts due to slippage. Therefore, deformation of the motion-compensation PET data due to the slippage is prevented.

According to an example embodiment, the determining slippage correction parameters is based on the first and second motion-compensated set of images.

By determining the slippage correction parameters based on the motion-compensated set of images, the slippage of one or more position markers can be accurately estimated.

The slippage correction parameters are derived by registering the motion-compensated set of images. The transformation obtained from the registration corresponds to the positioning error due to the slippage and represents the slippage correction parameters. Any type of intensity-based image registration is suitable, such as a rigid or a non-rigid (i.e. elastic or deformable) registration. Rigid registration is preferable when the subject's movement can be described as a translation and/or rotation, for example when performing a head scan. Deformable registration is preferred for example when performing an abdominal scan, i.e. when the subject deforms by expanding, collapsing, twisting, etc. Rigid registration is a less complex and therefore a faster registration than the elastic registration.

According to an example embodiment, the determining slippage correction parameters comprises masking the position markers in the first and second motion-compensated set of images and registering the first and second motion-compensated and masked set of images.

To correctly determine the slippage correction parameters, it is important that first, an intensity-based registration is performed rather than a feature-based registration, and, secondly, that the intensity-based registration is performed on the motion-compensated images with the position markers masked in the images.

Feature-based registration, for example registration based on the position markers will lead to obtaining incorrect slippage correction parameters for the following reasons. The position markers in the set before slippage will encompasses an area or volume representing one type of physiological and biochemical processes, while the set after slippage might encompass an area or volume representing another type of physiological and biochemical processer. In other words, the intensity in the two different areas or volumes encompassed by the position markers will change differently. As the registration will try to match these areas or volumes with different physiological and biochemical activities to each other, the outcome will be erroneous.

Similarly, if an intensity-based registration is performed without removing or masking the position markers in the images prior registration, the outcome of the registration will also be erroneous. This is because the intensity, i.e. the grey values, of the position markers is much higher than the intensity information of the scanned object, i.e. the intensity of the position markers will dominate in the intensity profile of the images, the intensity-based registration will try to match the regions with higher intensity in the images with each other, which will lead to a wrong registration.

According to an example embodiment, the method further comprising correcting the motion correction parameters with the slippage correction parameters.

This way, motion-compensated PET data free-from artefacts due to slippage is obtained.

According to an example embodiment, the method further comprising correcting scatter in the motioned-compensated PET data.

According to an example embodiment, the method further comprising:
    masking the position markers in the motion-compensated PET data, thereby deriving motion-compensated and masked PET data;
    deriving a PET scatter sinogram from the motion-compensated and masked PET data and scaling the PET scatter sinogram, thereby obtaining scatter corrected and motion-compensated PET data.

By masking the position markers in the motion-compensated PET data prior deriving the PET sinogram, it is guaranteed that the scatter sinogram will be correctly scaled to the PET sinogram.

According to a second example aspect, a data processing system comprising means for carrying out the method for motion compensation according to the present disclosure.

According to a third example aspect, a computer program product is disclosed, wherein the computer program product comprising computer-executable instructions for causing a system for correcting motion in positron emission tomographic, PET, data comprising coincident lines of response from positron-emitting position markers to perform the method according to the present disclosure.

According to a fourth example aspect, a computer-readable storage medium is disclosed comprising the computer program product according to the present disclosure.

BRIEF DESCRIPTION OF THE DRAWINGS

Some example embodiments will now be described with reference to the accompanying drawings.

FIGS. 5A and 5B show an example of a PET scatter sinogram corrected with a convention scatter correction.

DETAILED DESCRIPTION OF EMBODIMENT(S)

Figure 1:
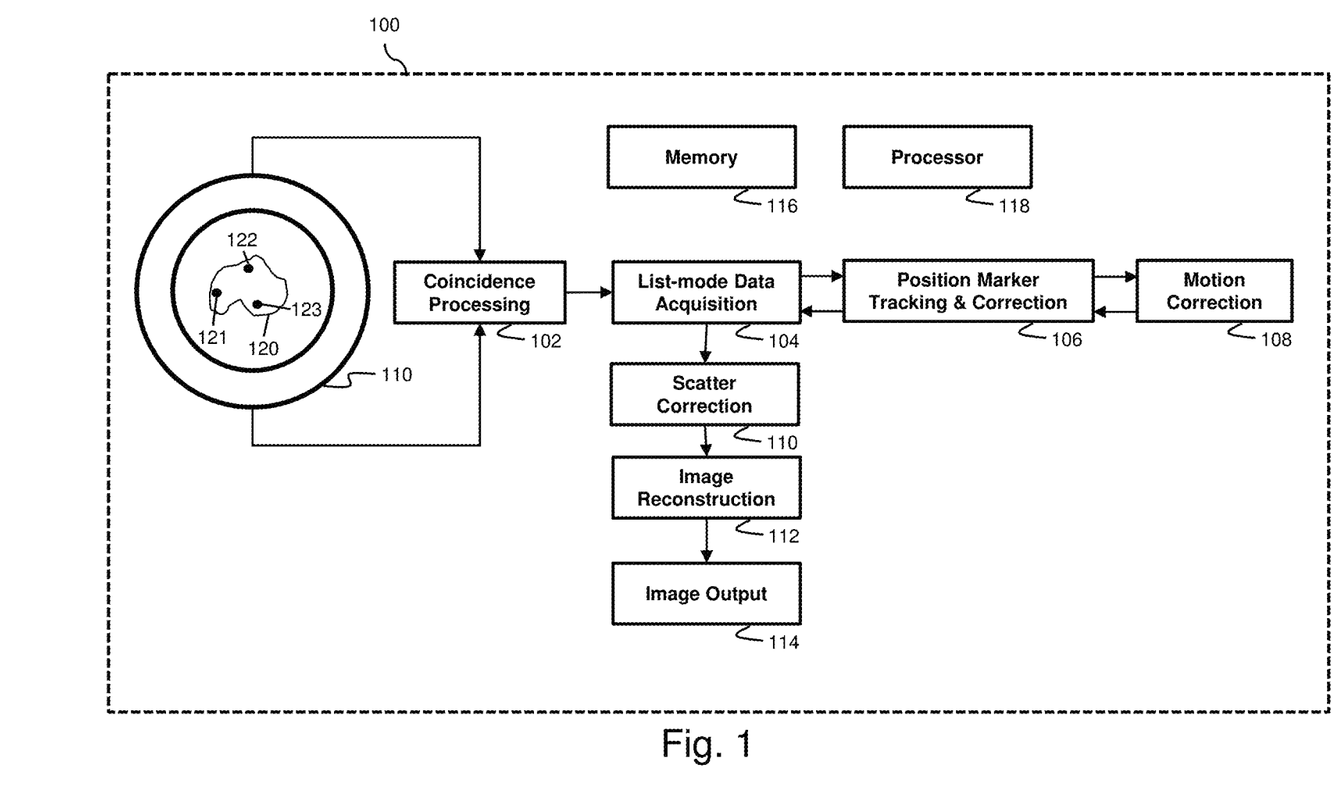
FIG. 1 shows an example embodiment of a PET imaging system according to the present disclosure.

FIG. 1 shows a simplified block scheme of a positron emission tomography, PET, imaging system 100 according to an embodiment of the present disclosure. The comprises a detector (not indicated), a coincidence processing module 102, a list-more data acquisition module 104, a position marker tracking and correction module 106, a motion correction module 108, a scatter correction module 110, an image reconstruction module 112, an image output module 114, a memory 116 and a processor 118. An object 120, for example a patient, is positioned inside the PET imaging device 110 and within the field of view of the detector, as shown in FIG. 1. The object may be moved horizontally depending on the region of interest of the object's that needs to be scanned, or imaged.

The memory may be a volatile memory, a non-volatile memory or a combination thereof. The memory may store program instructions, scan data generated by the PET imaging system 100 and any data as needed by the imaging system 100.

Algorithms to operate the coincidence processing module 102, the list-mode data acquisition module 104, the position marker tracking and correction module 106, the motion correction module 108, the scatter correction module 110, the imaging reconstruction module 112 and the image output module 114 are provided as software instructions stored in the memory 116. The processor 118 executes the instructions stored in the memory 116 and controls the operation of the PET imaging system 100, i.e. the operation of the coincidence processing module 102, the list-mode data acquisition module 104, the position marker tracking and correction module 106, the motion correction module 108, the scatter correction module 110, the imaging reconstruction module 112 and the image output module 114.

In some embodiments, the position marker tracking and correction module 106 and the motion correction module 108 may be provided internally or externally to the PET imaging system 100. Similarly, the scatter correction module 110 may be provided internally or externally to the PET imaging system 100. The image output module 114 may also be provided externally or internally to the PET imaging system 100. In such embodiments, the position tracking and correction module 106, the motion correction module 108, the scatter correction module 110 and the image output module 114 may include a separate memory and processor.

Figure 4:
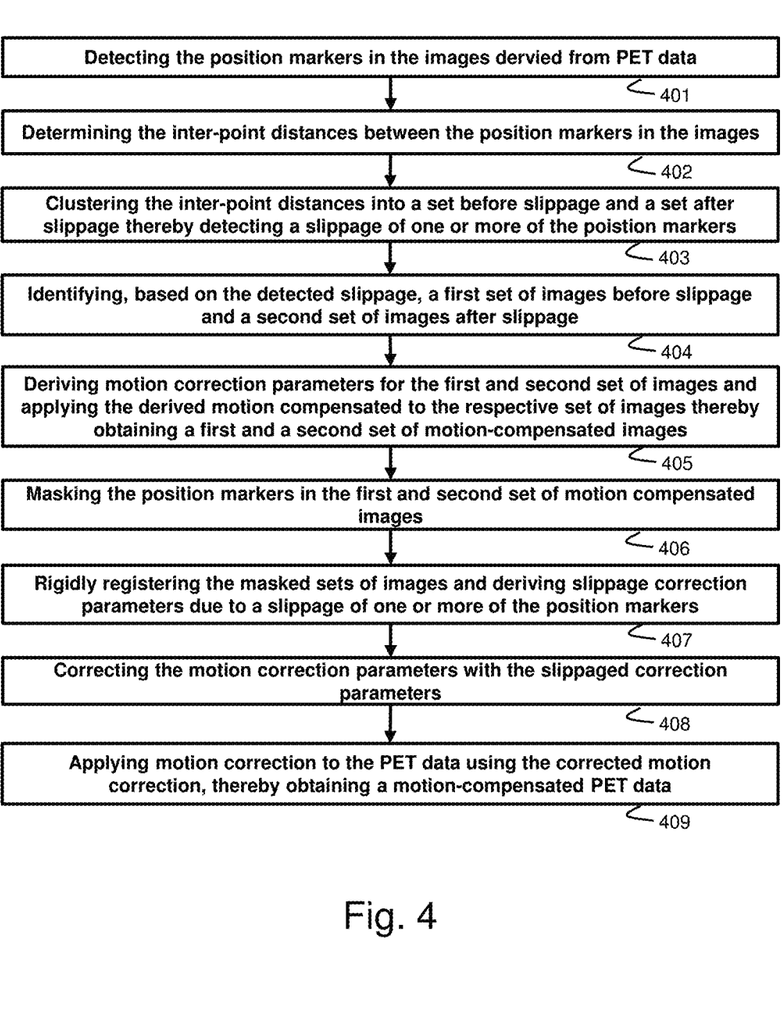
FIG. 4 shows a flow chart illustrating an example embodiment of the motion compensation method according to the present disclosure.

The method for compensating motion in PET data, according to an example embodiment of the present disclosure, will be explained below with reference to FIG. 4.

Figure 2A:
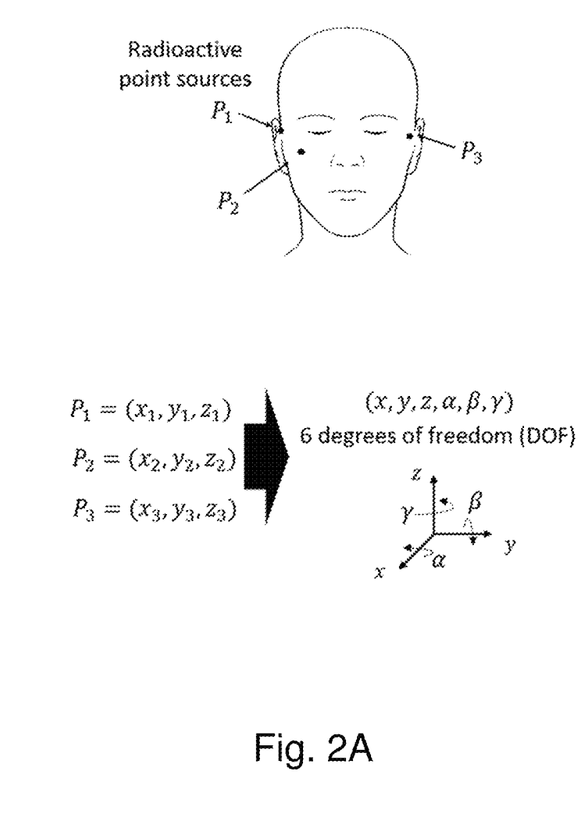
FIG. 2A shows PET position markers placed on the patient's head.

External emitting sources 121-123, such as positron emitting sources, and herein referred as position markers, are placed on the object of interest, e.g. the patient's head, as shown in FIG. 2A, for example. The position markers should be placed such that a three-dimensional tracking is enabled. For example, three position markers placed asymmetrically, i.e. placed in a non-collinear arrangement, may be used. More position markers could be also used. In that case, at least one of the position markers needs to be placed in a non-collinear arrangement with respect to the other position markers. Hence the placement requirements are more relaxed, which means that the placement of the position markers does not need to be performed by a trained medical professional. During the scanning, together with the pairs of annihilation photons emitted by the scanned object, pairs of annihilation photons from the position markers are detected by the detector and recorded among the list-mode data acquired by the list-mode data acquisition module 104.

The position marker tracking and correction module 106 uses the list-mode data from the list-mode acquisition module 104 to determine the coincident lines of response from the coincidence processing module 102 corresponding to the pairs of annihilation photons from the position markers 121-123. From the corresponding coincidence line of response, the tracking and correction module 106, tracks the position of the markers 121-123 in a three-dimensional space and records these locations throughout the course of the scan. This way, the location of the position markers in the PET data are detected (step 401) and then stored in the memory 116. Conventional image processing techniques suitable for detection of the location of the position markers 121-123 are well-known. For example, intensity-based image processing techniques can be applied to detect the local maxima points in the images. Due to presence of noise, low intensity local maxima points may also be detected. However, as the local maxima points corresponding to the position markers exhibit much higher intensity, the local maxima points due to noise can be easily removed by thresholding. The resulting image will then contain the local maxima points corresponding to the position markers.

The location of the position markers is represented by three coordinates along the x-, y- and z-axis. For example, a position marker located at position P1 has coordinates (x1, y1, z1), a position maker located at position P2 has coordinates (x2, y2, z2) and so on.

To derive the position of the position markers, the list-mode data needs to be converted into a volumetric image. The list-mode data is split into time frames with short duration, for example, a time frame can have a 32 ms duration, so that small movement could be identified. Therefore, the shorter the duration, the movements could be identified with a finer granularity. The shorter the duration, the higher the precision of the movement estimation and therefore the more complex subject's movement could be identified. For example, in case of sudden and/or complex movements time frames with a shorter duration are preferred.

The time frames are then reconstructed into volumetric images which together record the physiological and biochemical activity of the scanned subject over time. A complete reconstruction of the images is not required as these reconstructed images are used only for the detection of the position markers. Therefore, it suffices to perform an approximate reconstructed by applying a limited number of iterations of the list-mode expectation maximization algorithm. For example, it may suffice to reconstruct the image by applying 3 iterations. The reconstruction is therefore very fast.

Figure 2B:
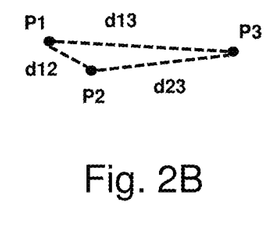
FIG. 2B shows the location of the position markers of FIG. 2A prior slippage.
Figure 2C:
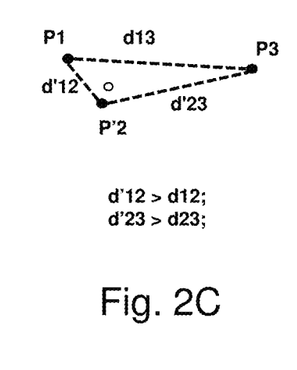
FIG. 2C show the location of the position markers of FIG. 2A after slippage.

For example, as shown in FIGS. 2B and 2C, marker 122 may slip from a position P2 with coordinates (x2, y2, z2) to a position P'2 with coordinates (x'2, y'2, z'2). Therefore, the inter-point distances between the second position marker 122 and the first and third position markers 121 and 123, respectively, changes from d12 and d23 to d'12 and d'23. In the example shown in the figure, d'12>d12 and d'23>d23.

After determining the locations of the position makers, the tracking and correction module 106, calculates the inter-point distances between the position markers in the images and clusters them into a first set before slippage and a second set after slippage.

To detect a slippage of one or more of the position markers, the distances among the position markers in the images are determined (step 402), i.e. the inter-point distances d12i, d13i and d23i where i denotes the image.

Figure 3:
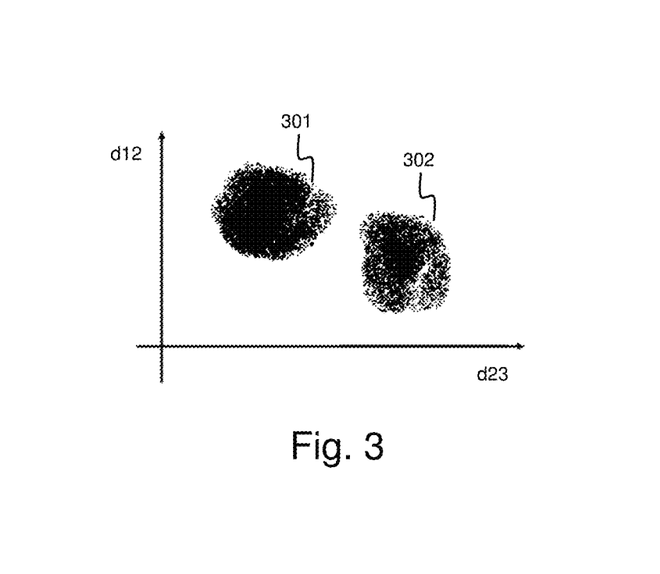
FIG. 3 shows an example of interpoint distances clustered according to the present disclosure.

The determined inter-point distances are then clustered (step 403) into a set before slippage and a set after slippage. FIG. 3 shows an example of two clearly separated clusters 301 and 302 indicating that the position marker 122 has slipped and the inter-point distances d12 and d23 have increased, where each point corresponds to the inter-point distances of an image. For simplicity, the figure shows only two dimensions (i.e. the inter-point distances d12 and d23) among all possible combinations. For example, when using three position markers there are three inter-point distances (d12, d13 and d23), and, when using four position markers, six inter-point distances (d12, d23, d34, d14, d13 and d24).

The two clusters are represented as a cloud, which indicates that the position of the position markers within a cloud are changing due to the movement of the subject during the scanning. Depending on the movement of the subject, the clouds could be bigger (or broader) or smaller (or more compacted). Depending on the amount of slippage, the clusters may be position closer to each other or more distantly. If the same position marker slips twice during the scanning, three clusters will be identified. If, however, the same position marker slips twice, but in this case it slips from a first position to a second position and then slips again from the second position back to the first position, then only two clusters will be identified although two slippages of the same position marker were observed. Thus, one cluster containing the distances among the position markers in the images before the first slippage and after the second slippage, and, another cluster containing the distances among the position markers in the images after the first slippage and before the second slippage will be created and identified.

The clustering algorithm labels each image according to the similarities in the inter-point distances in all images (step 404). Any interpoint distances greater or equal to two times the spatial resolution of the PET scanner may be classified as a slippage. Therefore, the differentiation between slippage and movement is dependent of the spatial resolution of the PET scanner. Therefore, the inter-point distances in all images within a cluster remain approximately in a rigid configuration as there is no slippage present among the images within the cluster. By labelling the images, two sets of images are identified, i.e. one set before slippage and another set after slippage.

The motion correction module 108 then estimates the motion correction parameters for a respective set of images (i.e. a cluster of images), by performing a registration. One way to do that is by performing a rigid registration, such as a point set registration, which involves calculation of the singular value decomposition of the cross-covariance matrix between the position of the position markers of each image within a respective set (or a cluster) to a position of the position markers selected as a reference position. For example, as a reference position, the position of the position markers in the first image within the set could be selected. Since the position markers in the images within a respective set did not slip with respect to each other, the approximate registration would not suffer from position marker slippage artefacts. Therefore, the point set registration will derive the motion correction parameters for a respective cluster free from any artefacts due to slippage and motion-compensated images per set will be obtained (step 405).

The tracking and correction module 106, then rigidly registers the motion-compensated set of images to derive the slippage compensation parameters (step 407). To do so, however, the position markers need to be masked (step 406) in the motion-compensated images prior registration. In other words, the grey value at the respective location of the position marker in the image is set to a predefined grey value. The tracking and correction module 106 retrieves the locations of the position markers from the memory 116 and masks the position markers in the motion-compensated set of images, thereby obtaining motion-compensated and masked set of images. These set of images are then rigidly registered. The rigid transformation obtained therefrom corresponds to the positioning error due to the slippage and represents the slippage correction parameters.

In the example where the same position marker slips twice from a first position to a second and then back to the first position, the motion correction module 108 will perform two registrations thus estimating two sets of motion correction parameters, one set of motion correction parameters for the first set of images, i.e. the images before the first slippage and the images after the second slippage, and another set for the second set of images, i.e. the images after the first slippage and before the second slippage. Similarly, the tracking and correction module 106 will derive the slippage correction parameters by registering the two motion-compensation and masked set of images as described above. Thus, in such cases, the clustering allows to group the distances among the position markers in an optimal way thus limiting the required number of registrations, and in this case, to the number of registrations required for a single slippage.

Alternatively, the slippage correction parameters may be derived based on one or more images from a respective motion-compensated set of images. For example, the last image or the last few images from the first motion-compensated set of images may be rigidly registered to the first image or the first few images of the second motion-compensated set of images. Another way to derive the slippage correction parameters may be by rigidly registering a first mean image derived from the first motion-compensated set of images and a second mean image derived from the motion-compensated second set of images. Performing rigid registration based on the mean images is preferred as the mean images are less noisy and therefore the rigid registration is faster.

The tracking and correction module 106 then corrects the motion correction parameters with the slippage correction parameters (step 408) and stores the updated motion correction parameters in the memory 116. The updated motion correction parameters are then used by the list-mode data acquisition module 104 to correct the list-mode data for the movement of the subject. A motion-compensated PET data is therefore obtained (step 409).

The image reconstruction module 112 then reconstructs the motion-compensated PET data thereby creating a reconstructed image which is outputted by the image output module 114.

Figure 7A:
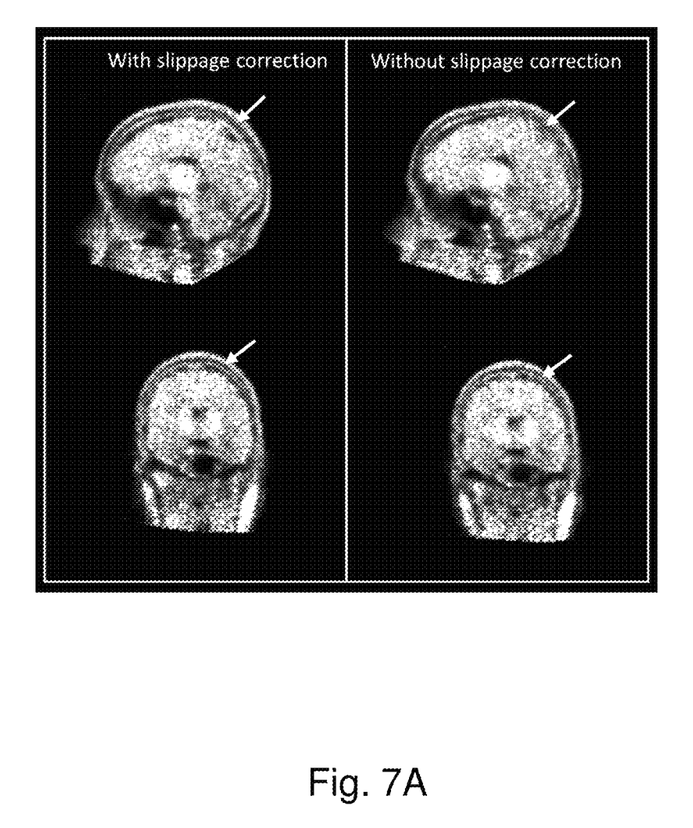
FIG. 7A shows an example of motion-compensated PET images using a conventional approach and motion-compensated PET images using the motion compensation with slippage correction according to the present disclosure.
Figure 7B:
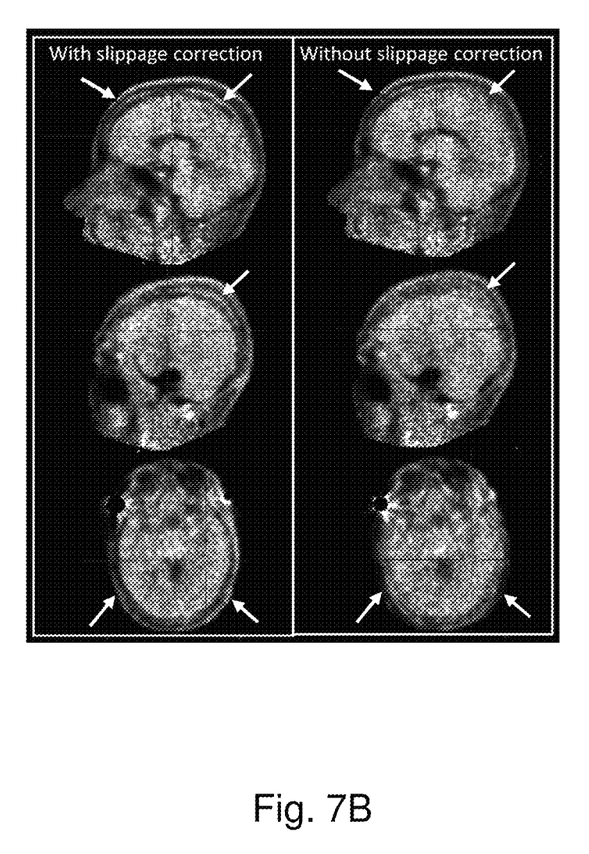
FIG. 7B shows another example of motion-compensated PET images using a conventional approach and motion-compensated PET images using the motion compensation with slippage correction according to the present disclosure.

FIGS. 7A and 7B show examples of reconstructed brain images with and without motion correction method according to the present disclosure. The arrows indicate visible artefacts due to the slippage of the position markers and their correction after applying the motion correction method according to the present disclosure. As it can be seen, the image quality is enhanced—the boundaries between different tissue structures are much better delineated which makes it easier to distinguish between them and therefore providing a higher diagnostic confidence.

Typically, prior image reconstruction, a scatter correction is performed by a scatter correction module 110. Scatter correction is done by estimating the occurrence of scatter events based on a simulation. The result is a scatter sinogram indicating the position and relative intensity of the scatter events. Sinograms are histograms in which each bin corresponds to a different line of response geometry, i.e. each having a different orientation and location. The intensity of the scatter sinogram is then scaled so that it corresponds to the intensity of the PET data. This is done by fitting the tails of the scatter sinogram to the PET sinogram.

Figure 5A:
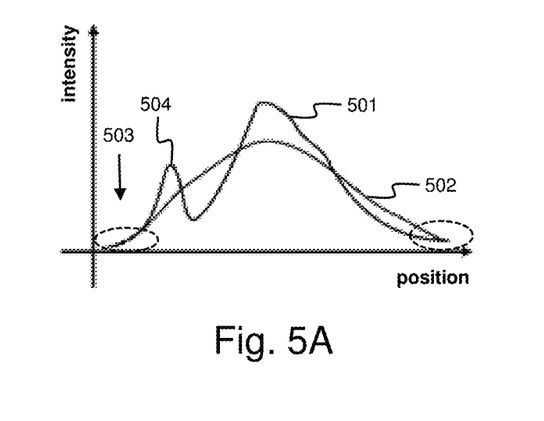

Position markers used for tracking the motion of the subject are however seen as high intensity regions in the PET sinogram. This causes the PET sinogram to present a high intensity peak at the borders as shown in FIG. 5A. When the scatter sinogram tail fitting is performed in such sinogram, the tail fit fails since the high intensity peak due to the position markers is also fitted to the scatter sinogram.

To perform a correct scatter correction, is therefore needed to remove the intensity peak due to the position markers. The scatter correction module 110 according to an embodiment of the present disclosure is arranged to retrieve the locations of the position markers from the memory 116.

Figure 6:
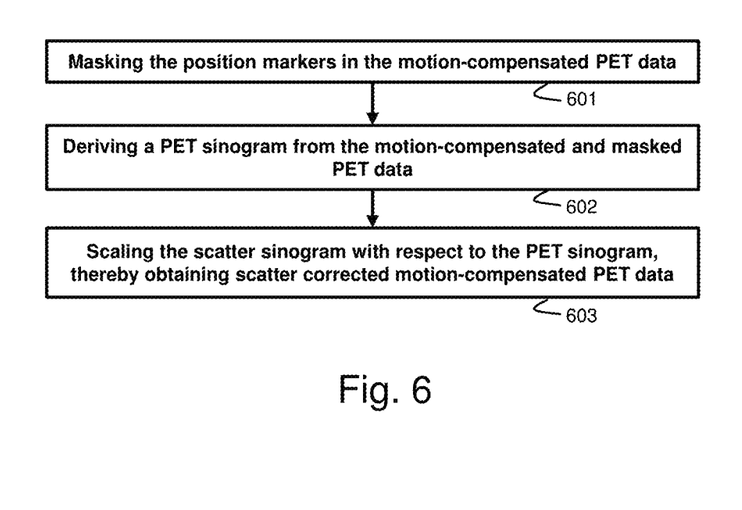
FIG. 6 shows a flow chart illustrating an example embodiment of the scatter correction method according to the present disclosure.

FIG. 6 shows the scatter correction procedure according to embodiments of the present disclosure. The scatter correction procedure described herein can be applied to any motion-compensated PET data with a motion compensation based on external emitting sources. The scatter correction procedure uses the location of the position markers to mask the lines of response in the PET data. The location of the position markers in the images have been already determined by the tracking and correction module 106 and corrected based on the determined motion correction parameters and the slippage correction parameters derived by the motion correction module 108 and the tracking and correction module 106, respectively. As these locations have been stored in the memory 116, the scatter correction module 110 can retrieve them directly therefrom. Using the retrieved locations, the scatter correction module 110, will mask 601 all lines of response (events) that pass within a pre-set threshold distance (for example 3 mm) near the position markers. From the resulting motion-compensated and now masked PET data, a PET sinogram is derived 602. The bins of the PET sinogram corresponding to these removed lines of response will have a value of zero. Alternatively, these lines of response are not removed but their number is set to a predetermined value, which once reconstructed has an image intensity of a soft tissue. The masked PET sinogram is then scaled 603 with respect to the simulate scatter sinogram to obtain a scatter corrected PET sinogram.

Figure 8:
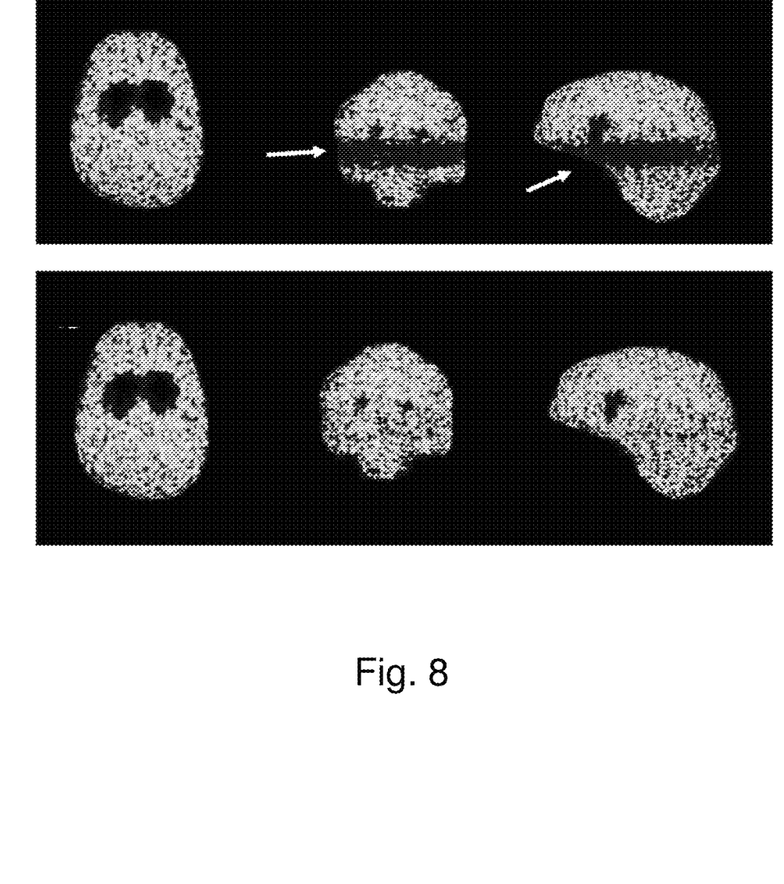
FIG. 8 shows examples of motion-compensated PET images with a conventional scatter correction and motion-compensated PET images with a scatter correction according to the present disclosure, respectively.

The top image in FIG. 8 shows the reconstruction of a motion corrected brain phantom when applying a conventional scatter correction. The lines of response corresponding to the pairs of annihilation photons emitted by the position markers results in high intensity regions in the reconstructed image. These high intensity regions affect the PET sinogram and produce high intensity regions or peaks in the PET sinogram. Sometimes they can be seen as an individual intensity peak 504 placed around the border (or tails) regions 503 in the PET sinogram as shown in FIG. 5A. Such a PET sinogram is however incorrectly fit (or scaled) to the scatter sinogram. The tails 503 of the PET sinogram are therefore wrongly fitted and seen as scatter events. The result of incorrect scatter correction is seen as lower intensity (activity) in the reconstructed image indicated by the arrows in top image in FIG. 8.

Figure 5B:
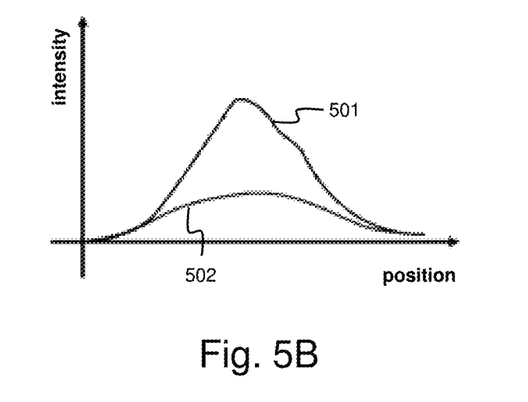
FIG. 5B shows an example of a PET scatter sinogram correction with the scatter correction according to the present disclosure.

The bottom image in FIG. 8 shows the reconstruction of a motion corrected brain phantom when the scatter correction according to the present disclosure is applied. Scatter sinogram scaled to the PET sinogram of a motion-compensated and masked PET data is shown in FIG. 5B. The PET sinogram contains only intensity information from the physiological and biochemical activities of the scanned subject and hence it does not exhibit intensity peaks caused by the position markers. As it can be seen in the bottom image in FIG. 8, the lower activity in the PET image is preserved and not seen as scatter events.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the scope of the claims are therefore intended to be embraced therein.

It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A method for compensating motion in positron emission tomographic, PET, data comprising coincident lines of response from positron-emitting position markers, the method comprising:
   detecting a slippage of one or more of the position markers;
   deriving a plurality of images from the PET data, and, identifying therefrom, based on the detected slippage, a first set of images before the detected slippage and a second set of images after the detected slippage;
   motion correcting the first and second set of images, thereby obtaining a first and a second motion-compensated set of images;
   determining slippage correction parameters based on the first and second motion-compensated set of images;
   applying motion correction to the PET data by taking into account the slippage correction parameters, thereby obtaining a motion-compensated PET data;
   correcting scatter in the motioned-compensated PET data;

masking the position markers in the motion-compensated PET data, thereby deriving motion-compensated and masked PET data; and deriving a PET scatter sinogram from the motion-compensated and masked PET data and scaling the PET scatter sinogram, thereby obtaining scatter corrected and motion-compensated PET data.

2. The method according to claim 1, wherein the identifying comprises determining locations of the position markers in the images and calculating therefrom inter-point distances between the position markers in the images.

3. The method according to claim 2, where the identifying further comprises clustering the calculated inter-point distances between the position markers in the images into a first set before slippage and a second set after slippage.

4. The method according to claim 3, wherein the clustering is based on a k-means algorithm or an expectation-maximization algorithm.

5. The method according to claim 1, wherein said motion correcting the first and second set of images further comprising:

deriving motion correction parameters for the first and second set of images;

applying the derived motion compensation parameters to the respective set of images, thereby obtaining the first and the second motion-compensated set of images from the respective first and second set of images.

6. The method according to claim 5, wherein the determining slippage correction parameters comprises masking the position markers in the first and second motion-compensated set of images and registering the first and second motion-compensated and masked set of images.

7. The method according to claim 6, further comprising correcting the motion correction parameters with the slippage correction parameters.

8. A data processing system comprising means for carrying out the method according to claim 1.

9. A non-transitory computer readable storage medium comprising a computer program product comprising computer-executable instructions for causing a system for correcting motion in positron emission tomographic PET, data comprising coincident lines of response from positron-emitting position markers to perform the method according to claim 1.

\* \* \* \* \*